United States Patent [19]

Schaeken et al.

[11] Patent Number: 5,178,870
[45] Date of Patent: Jan. 12, 1993

[54] ANTIMICROBIAL COMPOSITION WITH LONG-TERM ACTIVITY

[75] Inventors: Mathias J. M. Schaeken, Nijmegen; Johannes S. Van der Hoeven, Beek-Ubbergen; Pieter De Haan, Oss; Coenraad F. Lerk, Peize, all of Netherlands

[73] Assignees: Explore, Beek-Ubbergen; Rijksuniversiteit te Groningen, Groningen, both of Netherlands

[21] Appl. No.: 885,929

[22] Filed: May 18, 1992

Related U.S. Application Data

[63] Continuation of Ser. No. 573,005, Oct. 18, 1990, abandoned.

[30] Foreign Application Priority Data

Apr. 26, 1988 [NL] Netherlands ............. 8801087

[51] Int. Cl.⁵ .................. A61K 6/00; A61K 6/08
[52] U.S. Cl. .................. 424/405; 424/49; 424/52
[58] Field of Search ............. 424/49, 52, 405

[56] References Cited

U.S. PATENT DOCUMENTS

| | | | |
|---|---|---|---|
| 4,155,890 | 5/1979 | Hofacker-Freifrau | 523/115 |
| 4,496,322 | 1/1985 | Sandham et al. | 433/217.1 |
| 4,705,515 | 11/1987 | Wong et al. | 424/436 |

OTHER PUBLICATIONS

*The Merck Index,* 11th Ed., published by Merck & Co., Inc. Rahway, N.J., U.S.A., 1989, p. 1326.

*Primary Examiner*—Thurman K. Page
*Assistant Examiner*—Amy Hulina
*Attorney, Agent, or Firm*—Bachman & LaPointe

[57] ABSTRACT

The invention relates to an antimicrobial composition on the basis of a physiologically acceptable varnish dissolved therein an antimicrobial agent, preferably chlorhexidine, in an amount sufficient for elimination of Streptococcus mutans in one treatment. This composition can be applied on the tooth surface and other surfaces, such as the skin or on medical instruments.

15 Claims, No Drawings

ANTIMICROBIAL COMPOSITION WITH LONG-TERM ACTIVITY

This is a continuation of co-pending application Ser. No. 573,005 filed on Oct. 18, 1990 now abandoned.

The invention concerns an antimicrobial composition with long-term activity, comprising a physiologically acceptable varnish base and dissolved therein an antimicrobial agent.

Such a composition is known from IARD/AADR Abstracts 1985, abstract nr. 343. In this publication by H. J. Sandham et al. it is described that some antimicrobial varnish preparations with a controlled release of active material have been investigated in order to eliminate *Streptococcus mutans* from the dentition of a number of experimental subjects. It is generally accepted that *S. mutans* is the most cariogenic bacterial species. A varnish has been applied with 10% or 20% chlorhexidine acetate, erythromicin or penicillin in 10%, 20% or 40% Sumatra benzoin resin in ethanol. This resulted in a decrease of the number of *S. mutans* bacteria with a factor of maximally $10^5$; a complete elimination of *S. mutans* could not be achieved. Further, complete elimination could only be achieved if the chlorhexidine acetate containing varnish layer was covered with a top layer of a polyurethane varnish, and the whole procedure was repeated several times. After such a laborious procedure it was found that in 14 out of 33 experimental subjects the dentition remained free of *S. mutans* for an average period of 22.7 weeks (Sandham et al., J. Dent. Res. 67: 9–14 (1988) and IADR/AADR Abstracts 1988 nrs.930–932).

The application of antimicrobial dental varnishes is also described in a publication of T. E. Balanyk and H. J. Sandham in J. Dent. Res. 64 (12): 1356–1360 (1985). In this study varnishes containing 10% (weight/volume) chlorhexidine acetate or erythromycin base are used. As a resin base Sumarta benzoin resin is used. The aim of the research described in this publication, was to investigate whether *S. mutans* could be eliminated using a dental varnish with "unstained release" properties. The antimicrobial active substance is released from the resin matrix during a period of maximally about 14 days. It is stated, that in the first 24 hour after the treatment with varnish a relatively large amount of chlorhexidine acetate is released. This amount corresponds to 12 mg of chlorhexidine acetate in the oral cavity over a period of 24 hours.

From the above mentioned publications it appears, that Sandham et al. have tried to solve the problem of suppression of *S. mutans* by using the "slow release" properties of a dental varnish, that contains an antimicrobial agent, by which the active matrial is released in a delayed way. Because the varnish with 10 % or 20% chlorhexidine acetate was not effective enough for the longlasting elimination of *S. mutans* it was tried to improve the effect of the varnish by applying a top layer of a polyurethane varnish and by repeating the treatment.

According to the present invention it was surprisingly found that a longterm antimicrobial effect can be achieved after application of an antimicrobial preparation, as mentioned in the preamble, containing the antimicrobial agent in an amount sufficient to completely eliminate *S. mutans* on the dentition in a single treatment.

It was surprising to observe that after application of the preparation according to the invention, the return of *S. mutans* on the treated surface was strongly delayed, and the increase of caries was reduced.

According to the invention, the expression "elimination of *S. mutans*" means that the number of *S. mutans* bacteria is reduced to below the level of detection. This detection level is at least six times lower than the detection level of the method used by Sandham et al.

The preparation according to the invention is homogeneous and is generally liquid or gel-like and contains as antimicrobial agent preferably chlorhexidine or a salt thereof, for instance the acetate, in a quantity of more than 20% by weight, with respect to the weight of the complete preparation.

As varnish base a resin, dissolved in a solvent can be used. Both synthetic as well as natural resins can be used. Obviously, for dental applications the varnish base must be physiologically acceptable (for application onto skin or mucosa) and not cause negative taste preception. The antimicrobial agent used must be soluble in the varnish base. A suitable varnish base contains for example Sandarac, dissolved in ethanol. In principle, however, also other physiologically acceptable solvent, for example iso- or n-propanol can be used.

When chlorhexidine or a salt thereof, such as the acetate, is used as antimicrobial agent, this agent is present in a proportion of maximally 80% by weight, with respect to the weight of complete preparation. The preferred amount of antimicrobial agent is 30–50% by weight. An amount of less than 20% of the antimicrobial agent does not lead to a complete elimination of *S. mutans*. An amount of more than 80% does not offer extra advantages.

Using a composition according to the invention on the human dentition an amount of varnish of maximally about 250 mg is necessary for the treatment of the complete dentition; in practice, treatment will almost exclusively be restricted to fissures and interproximal spaces, which requires considerably less varnish, (approximately a quarter of the amount). A varnish containing 40% by weight of chlorhexidine acetate will release 100 mg of this antimicrobial agent over a period of 24 hours. This amount is considerably higher than the amount indicated by Sandham, which is 12 mg over a period of 24 hours. However, this is not taking into amount repetitive treatment such as applied by Sandham et al.

It is considered to be very surprising that such a relatively high amount of antimicrobial agent, such as chlorhexidine or a salt thereof, such as chlorhexidine acetate, is compatible with a varnish base, i.e. is completely dissolved.

It is assumed, that the favourable effect of the composition according to the invention is based on the fact that the return of *S. mutans* is delayed for a considerable period of time due to longterm activity of the preparation. It is likely that the sites of *S. mutans* in the ecosystem are occupied by other bacterial species, so that the return of *S. mutans* is impaired.

The composition according to the invention contains preferably a fluoride such as sodium fluoride, other fluorides than sodium fluoride are eligible too: e.g. stannous fluoride, aminfluoride and sodiummonofluorophosphate, because by using fluoride compounds the spectrum of activities of the preparation is enlarged. Fluoride serves to strengthen the hard tooth tissues against decalcification. Fluoride also has an additional effect on the suppression of *S. mutans*. The fluoride is preferably present in an amount of 0.1-1.0% by weight, with respect to the weight of the complete preparation. Other additives can be included in the preparation according to the invention too, for example triclosan, antibiotics, quaternary ammonium compounds, potassium nitrate.

The invention also relates to the preparation and the application of the antimicrobial compositions described.

A composition according to the invention can be applied not only for the suppression of caries on the tooth surface, but also on other surfaces, such as the skin, the nails, the mucosal surfaces or in body cavities as well as on medical instruments to be used on the above mentioned surfaces or in body cavities.

In the composition according to the invention the usual additives can be included, such as flavouring agents, aromatics and colouring agents, for example peppermint oil.

In the following examples the invention is further elucidated.

EXAMPLE I

A thin-liquid low viscosity varnish is prepared, consisting of
40% w/w chlorhexidine diacetate
27% w/w sandarac
33% w/w ethanol For the preparation of this varnish, first 30 g of sandarac is dissolved in 170 g ethanol. The solution is subsequently filtered through filter paper. Then 160 g of the filtrate is weighed and evaporated by heating to 40 g. Next 26.6 g of chlorhexidine diacetate is dissolved in the hot evaporated solution. The obtained solution is filled into tubes containing approximately 3 g of the varnish. The obtained varnish is thin-liquid and can easily be applied onto the tooth surfaces.

EXAMPLE II

A thick liquid high viscosity varnish consists of
40% w/w chlorhexidine diacetate
36% w/w sandarac
24% w/w ethanol This varnish is prepared in the same way as in example I.

EXAMPLE III

Protection of the dentition against caries by utilization of a dental varnish according to the invention.

Clinical research

Resins with chlorhexidine diacetate concentrations of 10%, 20% and 40% w/w were investigated as follows: volunteers were selected for the presence of high numbers of *S. mutans* in the fissures of the teeth. Their age varied from 20-25 years and the number of volunteers was 9. Fissures were selected as experimental surfaces because of the high caries susceptibility of these sites.

In each of the volunteers 3 fissures were selected and randomly distributed over 3 experimental groups. The fissures were treated with varnish that contained 10%, 20% or 40% chlorhexidine. The treatment implied that the fissure was dried by compressed air, after which a thin layer of resin was applied. After contact with saliva the resin sets within one minute. The rest of the dentition remained untreated. This design causes negative bias, with other words, the chances of finding a positive effect of the resin are diminished. This is so, because *S. mutans* from untreated sites could recolonize the treated fissures. The volunteers were asked not to clean the dentition in the 8 hours following the resin treatment. No further demands were made, or advice was given to the participants.

The effect of the treatment was determined on the total number of cultivable bacteria, and the numbers of *S. mutans, S. sanguis* and *A. viscosus/naeslundii* in plaque samples originating from the treated fissures. In addition, saliva samples were analyzed.

The results showed small variations in the number of bacteria in saliva. In fissures, a significant decrease of the total number of bacteria was only found 7 days after treatment with 40% chlorhexidine varnish. Treatment with varnish led to a strong suppression of *S. mutans*, the duration of the suppression of *S. mutans* in fissures was dependent upon the chlorhexidine concentration in the varnish. Table A gives the number of volunteers in whom *S. mutans* appeared to be completely absent at the indicated times following treatment with chlorhexidine resin. For a period of 3 weeks, *S. mutans* could not be demonstrated in the fissures of volunteers treated with 40% w/w chlorhexidine varnish. In the 10% and 20% chlorhexidine groups complete elimination of *S. mutans* was only observed in a limited number of volunteers. The mean values of *S. mutans* over the experimental period of 22 weeks show that the suppression in the 40% w/w chlorhexidine group lasted till the end of the experiment.

The varnishes had little effect on the numbers of *S.sanguis* and *A.viscousus/naeslundii* in the plaque samples. This is a favourable effect since these bacterial species interfere with the re-establishment of *S. mutans*.

Effect of chlorhexidine varnish on root surface caries

The effect of chlorhexidine varnish on the prevention of root surface caries was investigated in 30 patients surgically treated for periodontal diseases. The means age of the participants was 44 years. They were randomly distributed over two groups. In the chlorhexidine group all denuded root surfaces were treated with varnish (50% w/w chlorhexidine diacetate), the rest of the dentition remained untreated.

The varnish application was performed as described in the previous experiments, and the applications were repeated two times with intervals of three months. The patients in the control group were not treated with varnish. The clinical study was performed double blind.

Hard caries lesions were distinguished from soft carious lesions. The caries data were registrated at the start and at the end, one year after the first varnish treatment, of the experiment.

Table B gives the caries progression in both groups. The groups were not balanced with respect to the number of caries lesions at the beginning of the experiment: in the chlorhexidine group more caries was initially present, which indicates a higher caries activity in this group. After termination in the control group 21 new DF (decayed and filled) surfaces were found against 9 in the chlorhexidine group (p<0.01). The mean caries increment per subject was 1.5 in the control, and 0.56 in the chlorhexidine group, in spite of the higher caries activity in this last group.

Besides less new caries lesions, also a change in the consistency of the existing lesions occurred: in the control group 11% of the existing lesions became softer, i.e. caries extended, while another 11% had to be filled. In the chlorhexidine group on the other hand, 25% of the lesions became harder, which indicates a repair of the lesion (only 4% in the control group became harder), and only 4% of the existing lesions became softer.

TABLE A

Effect of varnishes containing chlorhexidine on *Streptococcus mutans* in fissures

| chlorhexidine concentration | Nr. of fissures with elimination of S.mutans (N = 9) weeks after treatment | | | | |
|---|---|---|---|---|---|
| | 1 | 3 | 6 | 12 | 22 |
| 10% | 5 | 5 | 2 | 2 | 1 |
| 20% | 6 | 6 | 3 | 3 | 2 |
| 40% | 9 | 9 | 8 | 6 | 5 |

TABLE B

Caries progression in two groups of patients

| | Number subjects | Nr.exposed root surfaces | Nr. of surfaces | | | |
|---|---|---|---|---|---|---|
| | | | decayed | | filled | |
| | | | 0 | 1 year | 0 | 1 year |
| control | 14 | 687 | 33 | 47 | 25 | 32 |
| chlorhexidine | 16 | 730 | 90 | 93 | 28 | 34 |

We claim:

1. Antimicrobial composition comprising a physiologically acceptable varnish base and as antimicrobial agent chlorhexidine or a salt thereof in an amount of more than 30% by weight based on the weight of the total composition, said amount being sufficient for elimination of Streptococcus mutans in one treatment.

2. The composition according to claim 1, characterized in that the varnish base is a natural resin dissolved in ethanol.

3. The composition according to claim 2, characterized in that the resin is sandarac.

4. The composition according to claim 1 characterized in that it contains chlorhexidine or a salt thereof in an amount of not more than 80% by weight based on the total composition.

5. The composition according to claim 1, characterized in that it contains chlorhexidine or a salt thereof in an amount of 30-65% by weight based on the total composition.

6. The composition according to claim 1, characterized in that it contains in addition fluoride, in the form of sodium fluoride, tin fluoride, amine fluoride, or sodium monofluoro phosphate.

7. The composition according to claim 6, characterized in that it contains the fluoride in an amount of 0.1-1.0% by weight based upon the total composition.

8. The composition according to claim 2, characterized in that it contains chlorhexidine or a salt thereof in an amount of not more than 80% by weight based on the total composition.

9. The composition according to claim 3, characterized in that it contains chlorhexidine or a salt thereof in an amount of not more than 80% by weight based on the total composition.

10. The composition according to claim 2, characterized in that it contains chlorhexidine or a salt thereof in an amount of 30-65% by weight based on the total composition.

11. The composition according to claim 3, characterized in that it contains chlorhexidine or a salt thereof in an amount of 30-65% by weight based on the total composition.

12. The composition according to claim 2, characterized in that it contains in addition fluoride, in the form of sodium fluoride, tin fluoride, amine fluoride, or sodium monofluoro phosphate.

13. The composition according to claim 3, characterized in that it contains in addition fluoride, e.g. in the form of sodium fluoride, tin fluoride, amin fluoride, or sodium monofluoro phosphate.

14. The composition according to claim 4, characterized in that it contains in addition fluoride, in the form of sodium fluoride, tin fluoride, amine fluoride, or sodium monofluoro phosphate.

15. The composition according to claim 5, characterized in that it contains in addition fluoride, in the form of sodium fluoride, tin fluoride, amine fluoride, or sodium monofluoro phosphate.

* * * * *